US010492983B1

(12) United States Patent
Sloan

(10) Patent No.: US 10,492,983 B1
(45) Date of Patent: *Dec. 3, 2019

(54) LINEAR MOTION MALE SEXUAL STIMULATION DEVICE

(71) Applicant: Brian Sloan, Mercer Island, WA (US)

(72) Inventor: Brian Sloan, Mercer Island, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/528,334

(22) Filed: Jul. 31, 2019

Related U.S. Application Data

(63) Continuation-in-part of application No. 16/373,529, filed on Apr. 2, 2019, which is a continuation of application No. 16/045,705, filed on Jul. 25, 2018, now Pat. No. 10,272,011.

(60) Provisional application No. 62/655,712, filed on Apr. 10, 2018.

(51) Int. Cl.

| | |
|---|---|
| ***A61F 5/00*** | (2006.01) |
| ***A61H 19/00*** | (2006.01) |
| ***A61H 1/00*** | (2006.01) |
| *A61H 23/02* | (2006.01) |

(52) U.S. Cl.
CPC ............... *A61H 19/32* (2013.01); *A61H 1/00* (2013.01); *A61H 23/0254* (2013.01); *A61H 2201/5023* (2013.01)

(58) Field of Classification Search
CPC ......... A61H 19/00; A61H 19/30; A61H 19/32
USPC ...................................................... 600/38–41
See application file for complete search history.

(56) References Cited

U.S. PATENT DOCUMENTS

2013/0281776 A1 10/2013 Levy
2016/0279020 A1 9/2016 Timmermans
2018/0140502 A1 5/2018 Shahoian et al.

*Primary Examiner* — John P Lacyk
(74) *Attorney, Agent, or Firm* — Brian R. Galvin; Brian S. Boon; Galvin Patent Law LLC

(57) ABSTRACT

An electromechanical device for male sexual stimulation that uses a reciprocal linear motion similar to sexual intercourse, and wherein the penis remains fully inserted during use. The reciprocal linear motion is generated by a small motor which drives a screw and nut mechanism, to which a bracket and gripper is attached. Inserted into the gripper is a flexible sleeve. A penis may be inserted into the device inside the flexible sleeve. The movement of the gripper and sleeve against the penis provides pressure and motion against the penis inside the sleeve in a manner similar to sexual intercourse. The speed, pattern, and location of the motion can be controlled by the user through controls on the outside of the device.

18 Claims, 23 Drawing Sheets

LINEAR MOTION MALE SEXUAL STIMULATION DEVICE

| CROSS-REFERENCE TO RELATED APPLICATIONS | | |
|---|---|---|
| Application No. | Date Filed | Title |
| Current application | Herewith | LINEAR MOTION MALE SEXUAL STIMULATION DEVICE<br>Is a continuation-in-part of: |
| 16/373,529 | Apr. 2, 2019 | LINEAR MOTION MALE SEXUAL STIMULATION DEVICE<br>which is a continuation of: |
| 16/045,705<br>Patent<br>10,272,011 | Jul. 25, 2018<br>Patent Date<br>Apr. 30, 2019 | LINEAR MOTION MALE SEXUAL STIMULATION DEVICE<br>which claims benefit of, and priority to: |
| 62/655,712 | Apr. 10, 2018 | LINEAR MOTION MALE SEXUGRIPPERION DEVICE |

the entire specification of each of which is incorporated herein by reference.

BACKGROUND

Field of the Art

The present invention is in the field of devices for sexual stimulation, and more particularly in the field of devices for male masturbation.

Discussion of the State of the Art

The following is a tabulation of some prior art that presently appears relevant:

| U.S. patent applications | | | |
|---|---|---|---|
| Document Number | Kind Code | Publication Date | Applicant |
| 20160279020 | A1 | 29 Sep. 2016 | KIIROO B.V. |

| Foreign Patent Documents | | | | |
|---|---|---|---|---|
| Document Number | Kind Code | Publication Date | Country Code | Applicant |
| 2777679 | A1 | 17 Sep. 2014 | EP | E-Process Consulting and Management 2013, S.L. |

There are various male sexual stimulation devices known in the prior art. The mechanisms by which stimulation is provided in these devices generally fall into one of five basic types: manual sheath mechanisms, vibratory mechanisms, suction mechanisms, constriction mechanisms, and direct electrical stimulation mechanisms. All of the existing mechanisms have one or more significant disadvantages, including non-ideal stimulation, possible release of bodily fluids, difficulty of use, and inability to customize the speed, pattern, and location of stimulation.

What is needed is a male masturbation device that provides a better user experience by providing optimal stimulation while eliminating the disadvantages of existing devices.

SUMMARY

Accordingly, the inventor has conceived and reduced to practice, according to a preferred embodiment, a linear motion male sexual stimulation device that provides a better user experience by providing an optimal linear stroking motion with optimal pressure, automation of the stroking motion, and user control over the speed, pattern, and location of the stroking motion, all while containing the penis and any bodily fluids fully inside the device.

According to a preferred embodiment, a male sexual stimulation device is disclosed, comprising: an axial reciprocal linear motion driver; a gripper attached to the axial reciprocal linear motion driver; and a flexible sleeve which is inserted into the gripper and which has a means for affixing the sleeve to the gripper, wherein a penis may be inserted into the flexible sleeve and remain fully inserted inside the device during stimulation, and wherein, when the device is activated, the inserted penis remains immobile inside the device while the gripper moves at least a portion of the sleeve affixed to the gripper in an axial reciprocating linear motion along the penis, providing sexual stimulation through pressure of the gripper against the penis contained in the sleeve combined with the axial reciprocal linear motion of the gripper and the portion of the sleeve affixed to the gripper.

According to an aspect of an embodiment, the linear motion driver comprises a threaded ball screw.

According to an aspect of an embodiment, the linear motion driver comprises a threadless ball screw.

According to an aspect of an embodiment, wherein the linear motion driver comprises a belt-driven linear actuator.

According to an aspect of an embodiment, the linear motion driver comprises a linear motor.

According to an aspect of an embodiment, the linear motion driver comprises a slider-crank.

According to an aspect of an embodiment, the linear motion driver comprises a hydraulic linear actuator.

According to an aspect of an embodiment, the linear motion driver comprises a pneumatic linear actuator.

According to an aspect of an embodiment, the flexible sleeve and gripper each comprise magnets, and the flexible sleeve is affixed to the gripper by magnetic attraction.

According to an aspect of an embodiment, the gripper further comprises a heating apparatus that warms the flexible sleeve to an optimal temperature.

According to an aspect of an embodiment, the gripper is an inflatable cavity that may be filled with a gas or a fluid.

According to an aspect of an embodiment, the gripper comprises a vibration mechanism that provides stimulation in addition to the linear motion stimulation.

According to an aspect of an embodiment, the device further comprises guide rods that guide the linear motion, the guide rods being configured such that each travel along the guide rods causes the gripper to partially rotate about a longitudinal axis parallel to the linear motion.

According to an aspect of an embodiment, the device further comprises a motor or actuator attached to the gripper mechanism and configured to rotate the gripper about a longitudinal axis parallel to the linear motion as it travels in a linear motion.

According to an aspect of an embodiment, the device further comprises: guide rods that guide the linear motion; a pivot installed at the bottom of the guide rods near the end of the device where a penis may be inserted; and a gear attached to the linear motion driver such that the linear motion causes the guide rods to tilt at the pivot, changing the direction of the linear motion during the linear motion along the guide rods.

According to an aspect of an embodiment, the device further comprises: guide rods that guide the linear motion; a pivot installed at the bottom of the guide rods near the end of the device where a penis may be inserted; and a separate motor, driver, or actuator which changes the pivot angle of the guide rods independently of the linear motion.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary, and are not to be considered as limiting of the scope of the invention or the claims herein in any way.

DETAILED DESCRIPTION

Figure 1:
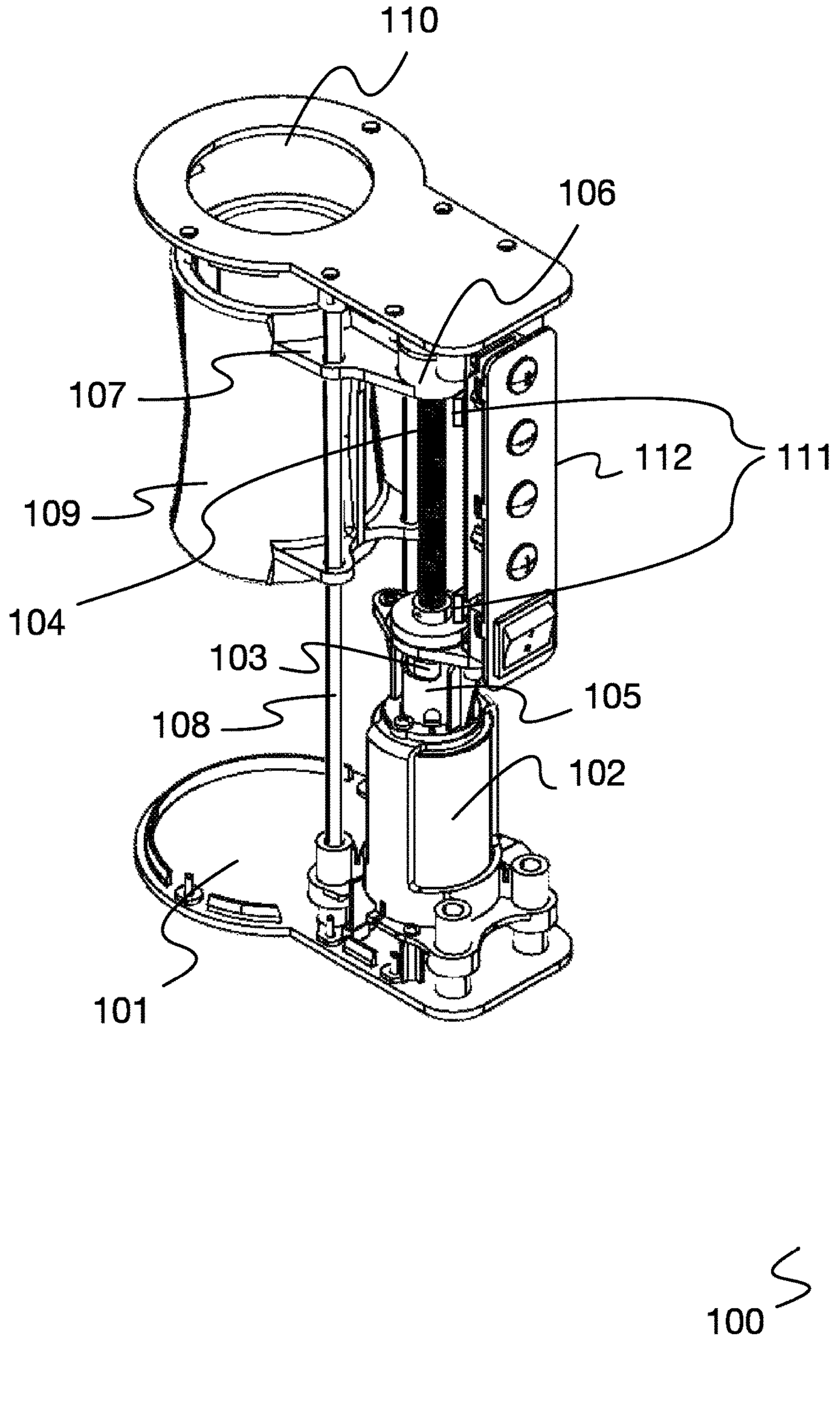
FIG. 1 shows the internal workings of an exemplary male sexual stimulation device according to a preferred embodiment.

The inventor has conceived, and reduced to practice, a linear motion male sexual stimulation device that provides a better user experience by providing an optimal linear stroking motion with optimal pressure, automation of the stroking motion, and user control over the speed, pattern, and location of the stroking motion, all while containing bodily fluids fully inside the device.

The mechanisms by which stimulation is provided in male sexual stimulation devices generally fall into one of five basic types: flexible sheath mechanisms, vibratory mechanisms, suction mechanisms, constriction mechanisms, and direct electrical stimulation mechanisms. Each of these devices has at least one significant disadvantage that is overcome by the present invention.

The sheath type device is tube-shaped device made of thermoplastic elastomer, thermoplastic rubber, silicone or other soft, flexible material, with or without an enclosing shell, into which the penis is inserted. The entire sheath device is moved up and down the shaft of the penis, causing stimulation by the friction and pressure of the sheath against the penis. Sheath type devices are used manually, requiring significant user effort, and possibly repetitive strain injury. They use a condom-like sleeve which can slip while in use, and either stretch, compress, or even slip off entirely and become lodged in the sheath. Sheath type devices expose the majority of the penis as the device is moved up and down the shaft of the penis, increasing the likelihood of release of bodily fluids outside of the device. Release of fluids outside of the device creates health and safety dangers to the user and others, can contaminate or damage other surfaces and materials onto which the fluids leak, and can make cleaning of the device itself difficult.

Vibratory mechanisms cause stimulation through oscillatory vibrations, usually created by an electric motor with an offset weight on the motor shaft. In many examples of vibratory mechanisms, for example the Hitachi Wand vibrator, the mechanism is simply pressed against the penis, causing stimulation by transmitting the vibration to the penis. In some forms of the vibratory mechanism, the penis may be inserted into the vibratory mechanism. Vibratory type devices provide a non-ideal type of stimulation, substituting vibration for the reciprocal linear motion of sexual intercourse. Further, most vibratory devices do not enclose the penis, and thus do not possess any method for containing bodily fluids. Vibratory mechanisms, in particular, also tend to produce substantial noise. While they sometimes allow the user to select different vibration patterns, such patterns do not provide much variance in stimulation, as they simply turn the device on and off at specified intervals.

Suction type devices are typically hard plastic tubes into which the penis is inserted at one end, and a suction pump is affixed to the other end. Suction type devices provide no direct stimulation through pressure or friction against the penis, and therefore provide substantially less than ideal stimulation. Suction devices may be combined with a sheath type mechanism.

A constriction type device is one in which the penis is inserted, and a set of rings either restrict blood flow back to the body, enhancing erection, or otherwise put inward radial pressure on the penis. Constriction type devices provide a non-ideal type of stimulation, substituting a squeezing motion for the reciprocal linear motion of sexual intercourse. Further, many constriction type devices do not enclose the penis, and thus do not possess any method for containing bodily fluids.

A direct electrical stimulation device is one in which the penis is stimulated through moderate voltage, very low current electrical shock. The electric shock stimulates nerve endings in the penis and may cause muscle contractions in surrounding tissue. The stimulation may be pulsed to provide different stimulation patterns. Direct electrical stimulation type devices provide a non-ideal type of stimulation, substituting electric shock pulses for the reciprocal linear motion of sexual intercourse. Further, most direction electrical stimulation type devices do not enclose the penis, and thus do not possess any method for containing bodily fluids.

The present invention overcomes the deficiencies in other mechanisms by providing ideal stimulation, similar in pressure and motion to that obtained during sexual intercourse or oral sex, in a device where the user can control the speed, pattern, and location of the motion, and where the penis remains fully enclosed in a hygienic sheath during stimulation. This device is substantially quieter than many of the alternatives, and provides substantially different stimulation in each of its user-selectable modes or patterns by allowing the user to choose where the stimulation should occur, how often it should occur at selected locations, and how fast it should occur at those locations.

The device may be controlled by an integrated circuit (IC) built into the device which controls the operation of the motor and monitors any sensors in the device. The IC may be pre-programmed or may, through a universal serial bus (USB) or other interface, be user programmable using a computer application. In either case, the IC may control the operation of the device by adjusting motor speed and direction to implement the patterns of stimulation programmed into the IC. Sensors in the device may be used to set limits of motion of the nut and screw mechanism, to ensure that the mechanism is at one end of its range of motion prior to operation, or to detect and protect against other device parameters such as motor over-heating. Sensors may be of any type suitable for the purpose, including but not limited to electrical contacts, magnetic sensors, magnetic reed switches, mechanical switches, rotational sensors, optical sensors, and temperature sensors.

In a preferred embodiment, the rotary motion from a small electric motor is translated to a linear motion through the use of a screw shaft and nut. The linear motion is translated into penile stimulation by a gripper that provides pressure against the penis through the sleeve as it glides up and down the shaft of the penis. Bodily fluids are contained within a flexible sheath inserted into the gripper, and into which the penis is inserted during use. This differs from sheath type devices in that the penis remains fully inserted in the device while in use, and the device itself is not drawn up and down the penis as with sheath type devices.

In some embodiments, the linear motion may be provided by other linear motion mechanisms. A non-exhaustive list of linear motion mechanisms that could be used in certain embodiments includes: ball screw mechanism, belt-drive linear actuator, linear motor, slider-crank mechanism, and hydraulic or pneumatic linear actuator. The use of these other linear motion mechanisms in certain embodiments will be described herein. Generally speaking, any mechanism capable of generating a linear motion could be used.

In some embodiments, the gripper mechanism may take a variety of alternate forms. A non-exhaustive list of alternative gripper mechanisms that could be used in certain embodiments includes: tubular gripper, annular (ring) gripper, partial-tube or partial-ring gripper, loop or band gripper (including loops and bands made of wire, plastic, metal, or other materials, and including multiple loops or bands), magnetic gripper, gripper with built-in heating elements, inflatable gripper, and vibrating gripper, a gripper with leaf springs or flexible plastic tines. The use of these other gripper mechanisms in certain embodiments will be described herein. It is important to note that the gripper is not limited to mechanisms or structures that “grip” by providing radial inward pressure (for example, leaf springs or flexible plastic tines), although such structures can be used. Generally speaking, any mechanism or structure to which a flexible sleeve may be affixed and which is capable of providing friction against a penis during linear motion may be used as a gripper.

In some embodiments, the linear motion may be augmented with a rotational motion of the gripper. For example, the guide rods supporting the gripper along which the linear motion occurs could be tilted or configured in a spiral, such that each travel along the guide rods causes the gripper to partially rotate about a longitudinal axis parallel to the linear motion. Alternatively, a motor or actuator could be attached to the gripper mechanism to rotate the gripper about a longitudinal axis parallel to the linear motion as it travels in a linear motion.

In some embodiments, the linear motion may be augmented by changing the direction of the linear motion. For example, a pivot could be installed at the bottom of the guide rods, and a gear attached to the linear motion driver such that the linear motion causes the guide rods to tilt, changing the direction of the linear motion during each travel along the guide rods. Alternatively, a separate motor, driver, or actuator could be installed, which changes the pivot angle of the guide rods independently of the linear motion.

Figure 2:
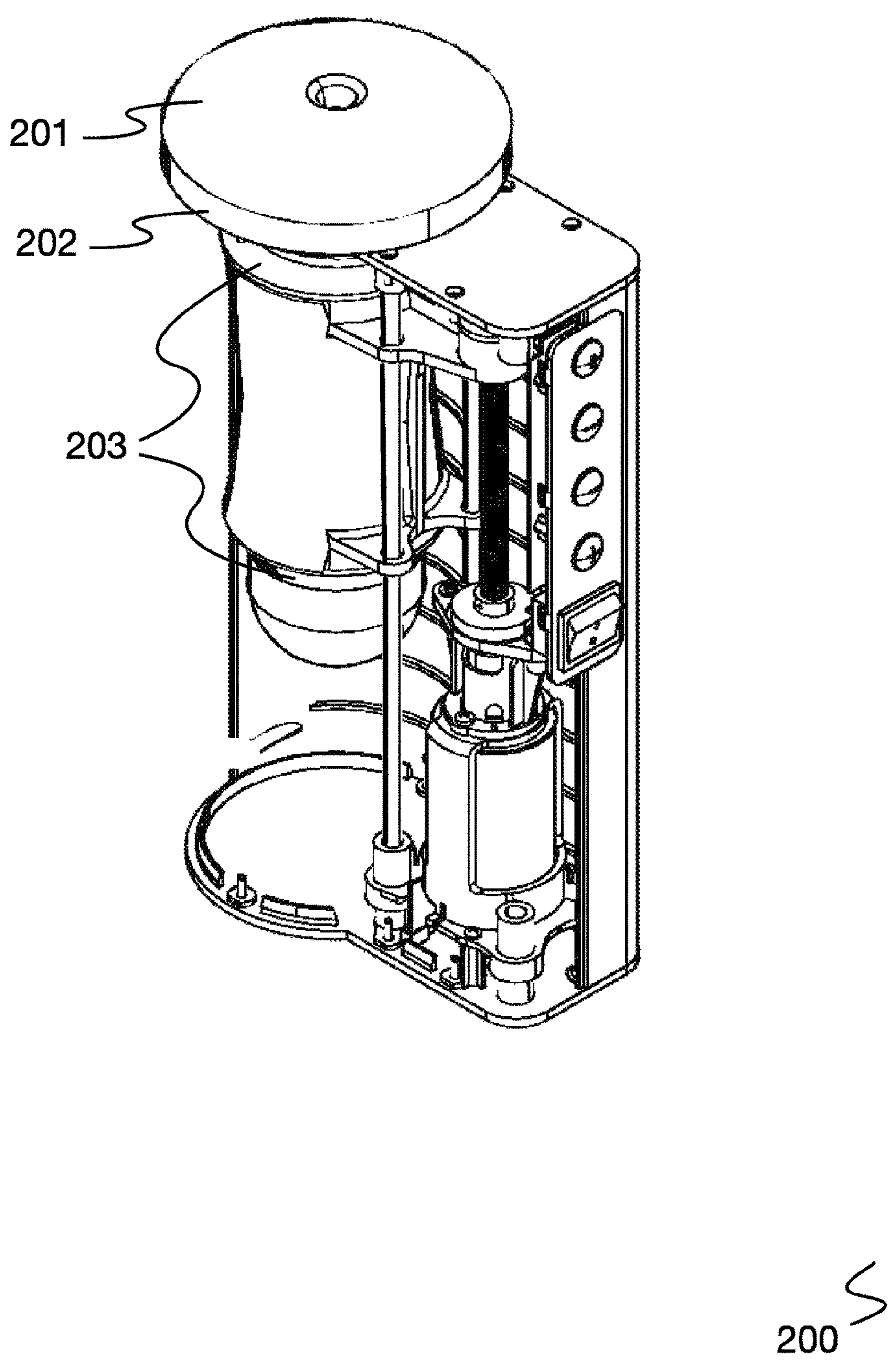
FIG. 2 shows additional components of the internal workings of an exemplary male sexual stimulation device as set forth in a preferred embodiment.

FIG. 1 shows the internal workings of an exemplary male sexual stimulation device 100 according to a preferred embodiment. In this embodiment, the device is a small handheld unit powered by a low voltage, external direct current (DC) power source. Inside the device is a framework 101 to which the mechanical parts of the device are attached. Attached to the framework 101 is a small DC motor 102 with a motor shaft 103, which drives the stimulation mechanism. A screw shaft 104 is affixed to the motor shaft 103 of the DC motor 102, such that the screw shaft 104 rotates as the motor shaft 103 of the DC motor 102 rotates. The polarity of voltage to the DC motor 102 may be reversed so that the motor shaft 103 of the DC motor 102 rotates both clockwise and counter-clockwise. A flex coupling 105 between the motor shaft 103 of the DC motor 102 and screw shaft 104 compensates for any misalignment between the two during operation. A nut 106 is placed around the screw shaft 104 and attached to a bracket 107, which is held in a particular orientation by guide rods 108, such that the nut 106 and bracket 107 travel in a linear motion as the screw shaft 104 is turned. Affixed to the bracket 107 is a gripper 109, which travels in a linear motion along with the bracket 107. A hole 110 in the framework 101, allows for the insertion of a flexible sleeve as shown in FIG. 2. Magnetic sensors 111 may be used to set limits of operation of the nut 106, or to ensure that the nut 106 is at one end of its range of motion before starting operation of the device. An integrated circuit (not visible in drawing) 112 may be used to control the operation of the device.

FIG. 2 shows additional components of the internal workings of an exemplary male sexual stimulation device 200 as set forth in a preferred embodiment. A flexible sleeve 201 made of either thermoplastic elastomer (TPE) or thermoplastic rubber (TPR) or silicone is inserted through a hole 110 in the framework 101 and through gripper 109. Sleeve 201 is prevented from accidentally slipping into device 200 by a ridge 202 at the open end of sleeve 201, and is held in the proper position by ridges 203 on the sleeve 201 at both ends of gripper 109. During operation, gripper 109 slides in a reciprocal linear motion 201 providing pressure and motion against the penis inside the sleeve 201 in a manner similar to sexual intercourse or manual masturbation. Depending on the configuration, gripper 109 may either grip sleeve 201 and move sleeve 201 along the penis, or it may slide along the outside of sleeve 201, not moving the sleeve relative to the penis. Also depending on configuration, gripper 109 may be made of rigid, semi-rigid, or compliant materials, and other shapes might be used (e.g., partial tube, ring, half-ring, multiple rings, loops of wire) and may contain rollers or bearings to increase stimulation and reduce friction against the flexible sleeve 201.

Figure 3:
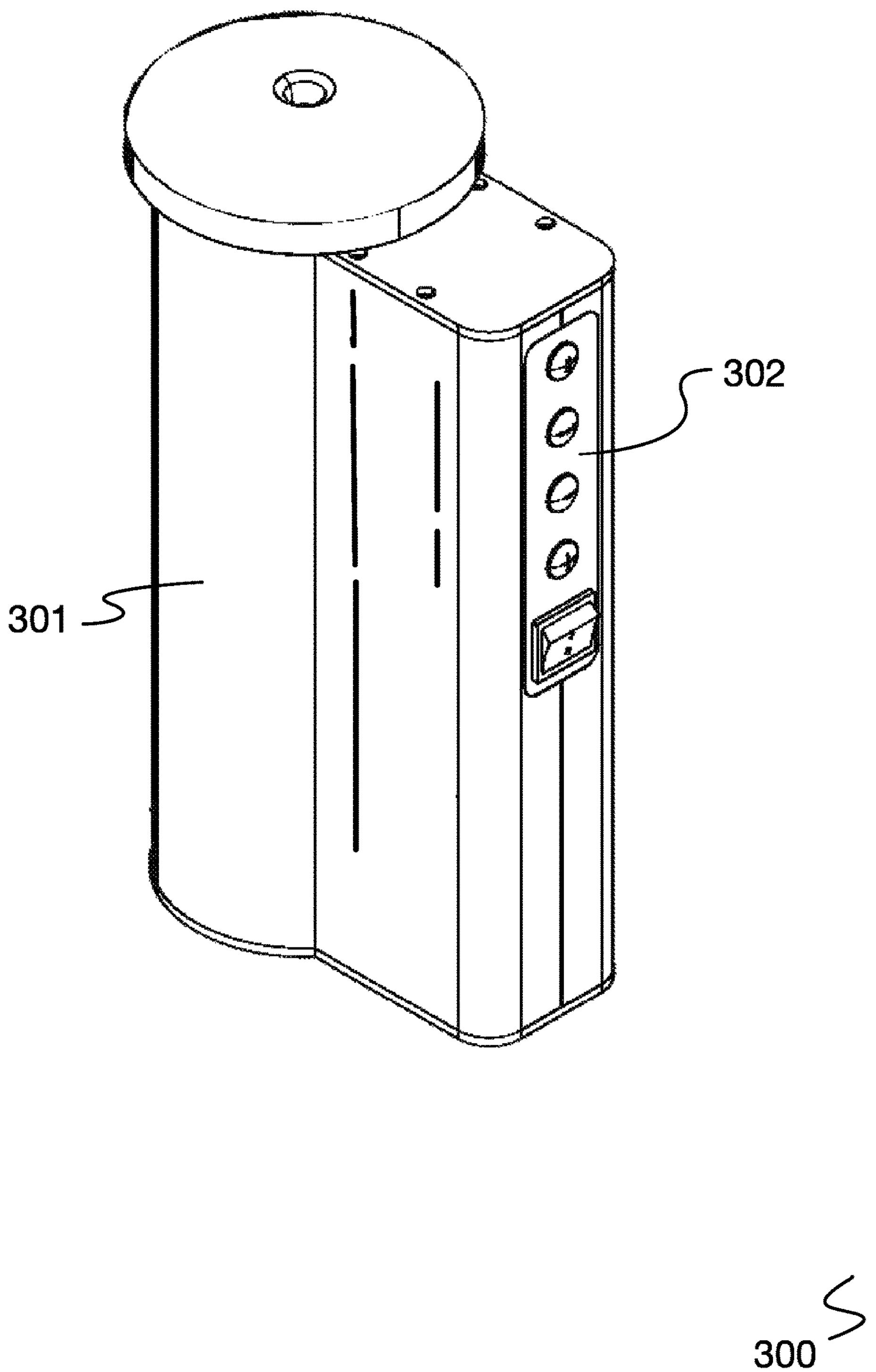
FIG. 3 shows the external structure of an exemplary male sexual stimulation device.

FIG. 3 shows the external structure 300 of an exemplary male sexual stimulation device. The housing 301 of the device is made of plastic, and is attached to the framework in such a way as to provide additional support and structure to the device. User controls 302 in the form of buttons and switches and their associated electronics are built into the housing. The housing has an opening at one end corresponding to the opening 110 in the framework 101, into which the flexible sleeve 201 is inserted. The penis is inserted into the sleeve 201 at the end of the device, and is stimulated by the reciprocal linear motion of the gripper 109 inside the device. The user controls the speed, pattern, and location of stimulation using the controls 302 on the outside of the housing 301.

Figure 4:
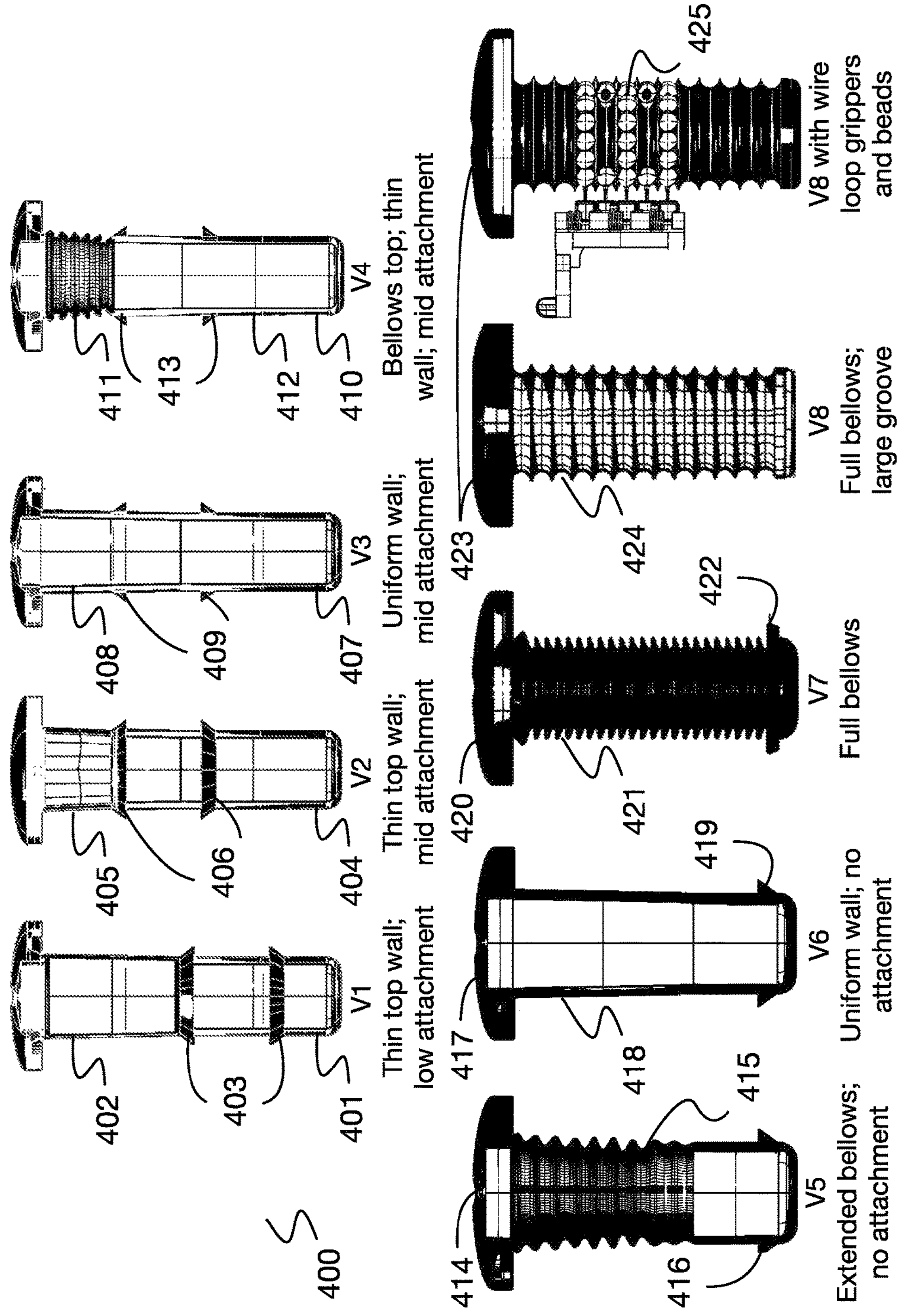
FIG. 4 shows exemplary variations of the sleeve and gripper aspects of an exemplary male sexual stimulation device.

FIG. 4 shows exemplary variations 400 of the sleeve 201 and gripper 109 aspects of an exemplary male sexual stimulation device. As noted above, different configurations of the sleeve 201 and gripper 109 are possible to allow optimal fit and sensation for penises of different lengths and girths, and to allow the user a choice of pressure, gripper location, and sensation. Sleeve variant one 401 has a thin top wall 402 with a low point of attachment 403 to the gripper 109. Sleeve variant two 404 has a thin top wall 405 with a middle point of attachment 406 to the gripper 109. Sleeve variant three 407 has a uniform wall thickness 408 with a middle point of attachment 409 to the gripper 109. Sleeve variant four 410 has a bellows top 411, a thin wall 412, and a middle point of attachment 413. Sleeve variant five 414 has an extended bellows 415 and no attachment to the gripper 109 other than a stopper at the end 416, allowing the gripper 109 to slide along the outside of the sleeve 414. Sleeve variant six 417 has a uniform wall thickness 418 and no attachment to the gripper 109 other than a stopper at the end 419, allowing the gripper 109 to slide along the outside of the sleeve 417. Sleeve variant seven 420 has a full bellows design 421 and no attachment to the gripper 109 other than a stopper at the end 422, allowing the gripper 109 to slide along the outside of the sleeve 420. Sleeve variant eight 423 has a full bellows design with large grooves 424 into which fits a gripper made of wire loops with beads attached 425.

Figure 5:
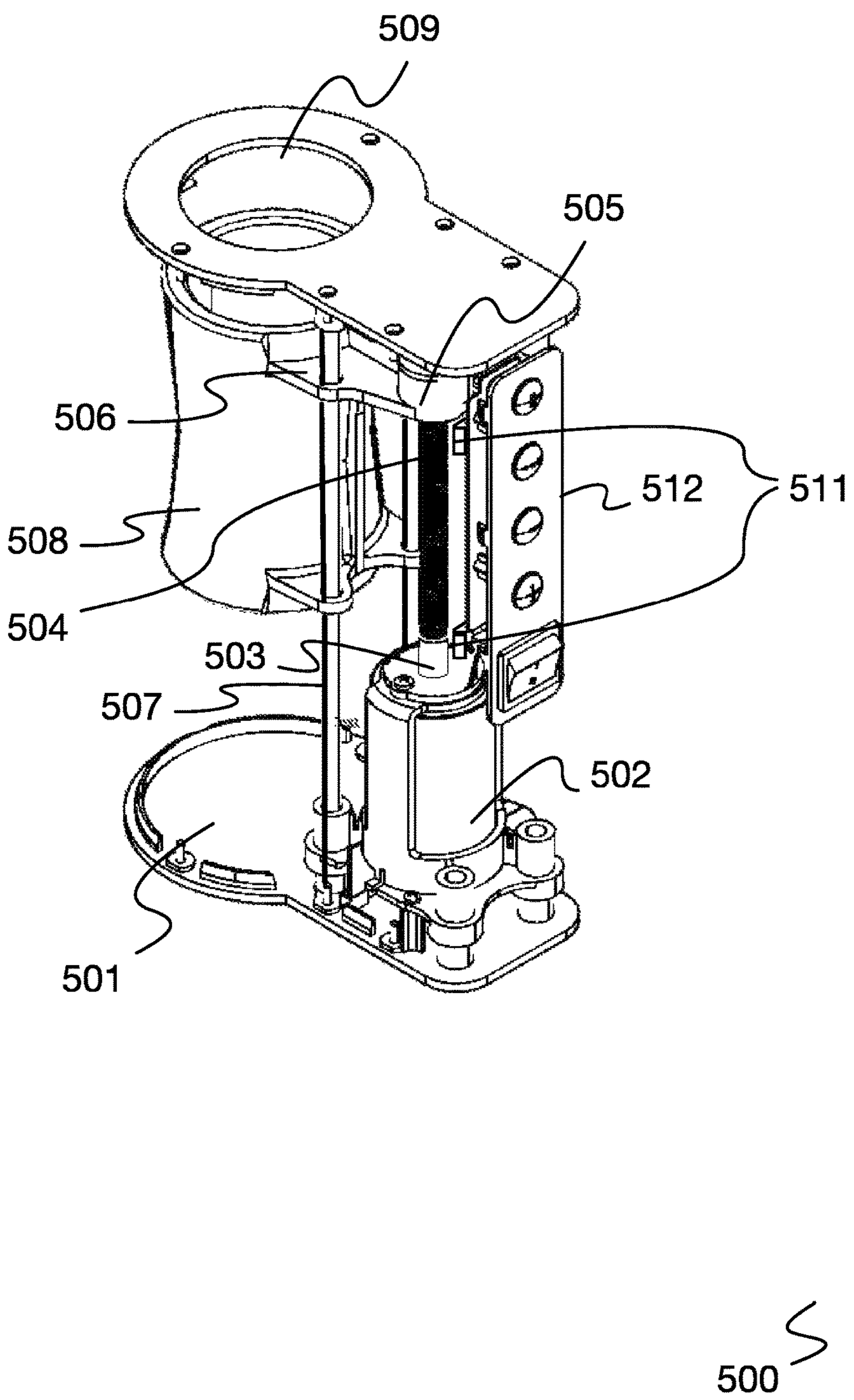
FIG. 5 shows the internal workings of an exemplary male sexual stimulation device according to another preferred embodiment.

FIG. 5 shows the internal workings of an exemplary male sexual stimulation device 500 according to another preferred embodiment. In this embodiment, the device is a small handheld unit powered by a low voltage, external direct current (DC) power source. Inside the device is a framework 501 to which the mechanical parts of the device are attached. Attached to the framework 501 is a small DC motor 502 with a motor shaft 503, which drives the stimulation mechanism. A screw shaft 504 is affixed directly to the motor shaft 503 of the DC motor 502, such that the screw shaft 504 rotates as the motor shaft 503 of the DC motor 502 rotates. The polarity of voltage to the DC motor 502 may be reversed so that the motor shaft 503 of the DC motor 502 rotates both clockwise and counter-clockwise. In this embodiment, the flex coupling 105 has been eliminated, allowing the device to be constructed in a more compact form, approximately 2 cm shorter in overall length. A nut 505 is placed around the screw shaft 504 and attached to a bracket 506, which is held in a particular orientation by guide rods 507, such that the nut 505 and bracket 506 travel in a linear motion as the screw shaft 504 is turned. Affixed to the bracket 506 is a gripper 508, which travels in a linear motion along with the bracket 506. A hole 509 in the framework 501, allows for the insertion of a flexible sleeve 201 as previously shown in FIG. 2. Magnetic sensors 511 may be used to set limits of operation of the nut 506, or to ensure that the nut 506 is at one end of its range of motion before starting operation of the device. An integrated circuit (not visible in drawing) 512 may be used to control the operation of the device.

Figure 6:
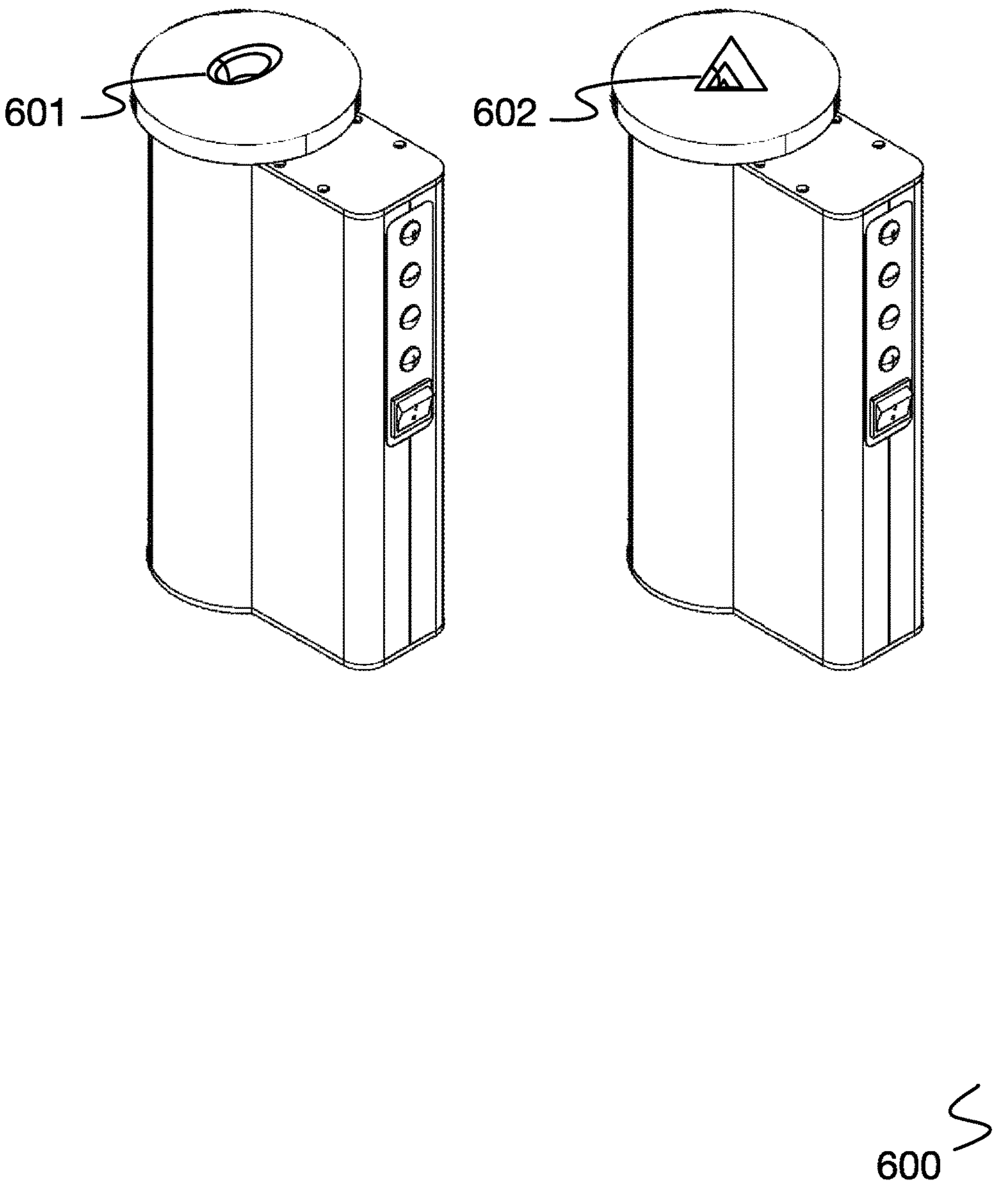
FIG. 6 shows additional exemplary variations of the sleeve aspect of an exemplary male sexual stimulation device.

FIG. 6 shows additional exemplary variations 600 of the sleeve aspect of an exemplary male sexual stimulation device. In this embodiment, the opening in the sleeve may be other than circular. For example, the opening may be elliptical in shape 601 or triangular in shape 602.

Figure 7:
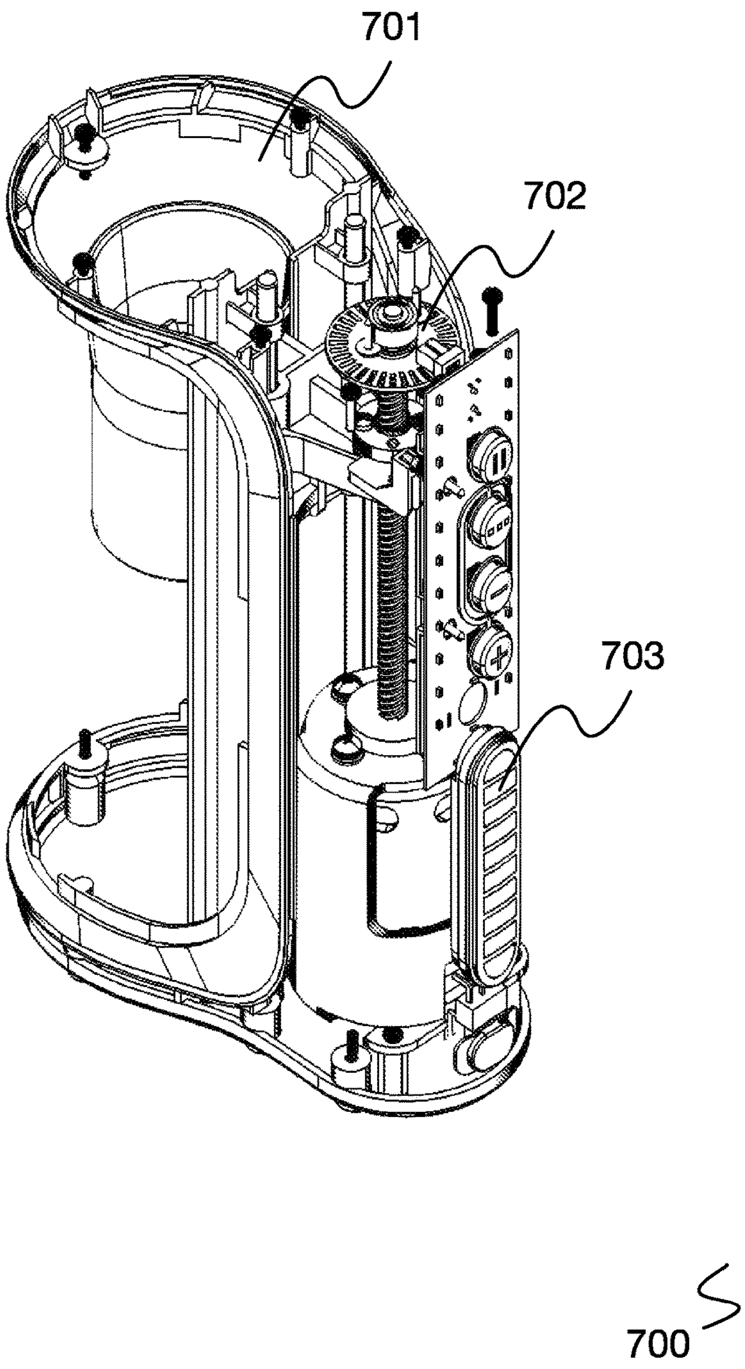
FIG. 7 shows an aspect of an embodiment of male sexual stimulation device according to another preferred embodiment.

FIG. 7 shows an aspect of an embodiment of male sexual stimulation device according to another preferred embodiment 700. In this embodiment, the framework 701 is made from a molded plastic structure. An optical rotary encoder 702 is used to determine the rotational speed and number of rotations of the screw shaft to control patterns of stimulation. A series of light emitting diodes (LEDs) 703 are used to indicate the mode of operation of the device.

Figure 8:
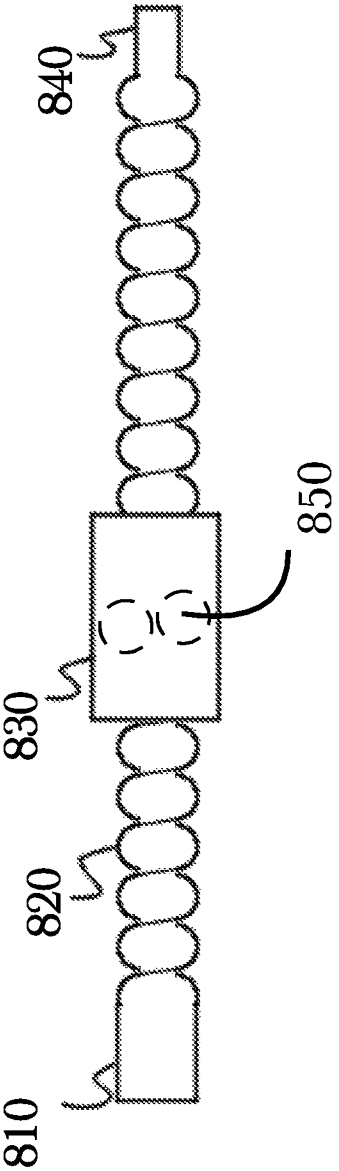
FIG. 8 shows an aspect of an embodiment of male sexual stimulation device comprising a ball screw mechanism.

FIG. 8 shows an aspect of an embodiment of male sexual stimulation device comprising a ball screw mechanism. A ball screw mechanism may be used to translate rotational motion to linear motion and comprises a threaded shaft 820 with two ends 810, 840, a ball assembly 830 containing a plurality of ball bearings 850 set at an angle equal to the angle of the threads on the shaft, which allow a rotation along a threaded body 820 to translate into linear motion. A ball screw mechanism may be used as a linear motion driver. Ball screws are useful because they can withstand large thrust loads with minimum internal friction. Variations on this mechanism include the threadless ballscrew (also known as a rolling ring drive) wherein the shaft is threadless, and a series of bearings are set at an angle in a housing around the shaft, the angle determining the rate of linear motion per revolution of the rod.

Figure 9:
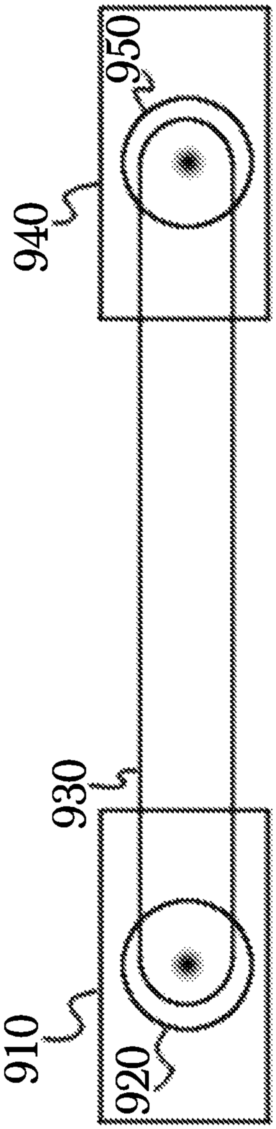
FIG. 9 shows an aspect of an embodiment of male sexual stimulation device comprising a belt-drive linear actuator.

FIG. 9 shows an aspect of an embodiment of male sexual stimulation device comprising a belt-drive linear actuator. A belt-drive linear actuator may be used to produce linear motion through the use of two spinning wheel-like devices 920, 950 built into housing with motors 910, 940 to spin, causing linear motion of a belt wrapped around both wheels 930, allowing for linear motion in two directions, depending on the examined side of the belt, and depending further on the direction in which the wheels 920, 950 are spinning. In this way, a belt-driven linear actuator may be an alternative method for moving a gripper 109 up or down. Some belt-drive linear actuators have a single motor at one end and a free-spinning pulley at the other end, instead of motors at both ends.

Figure 10:
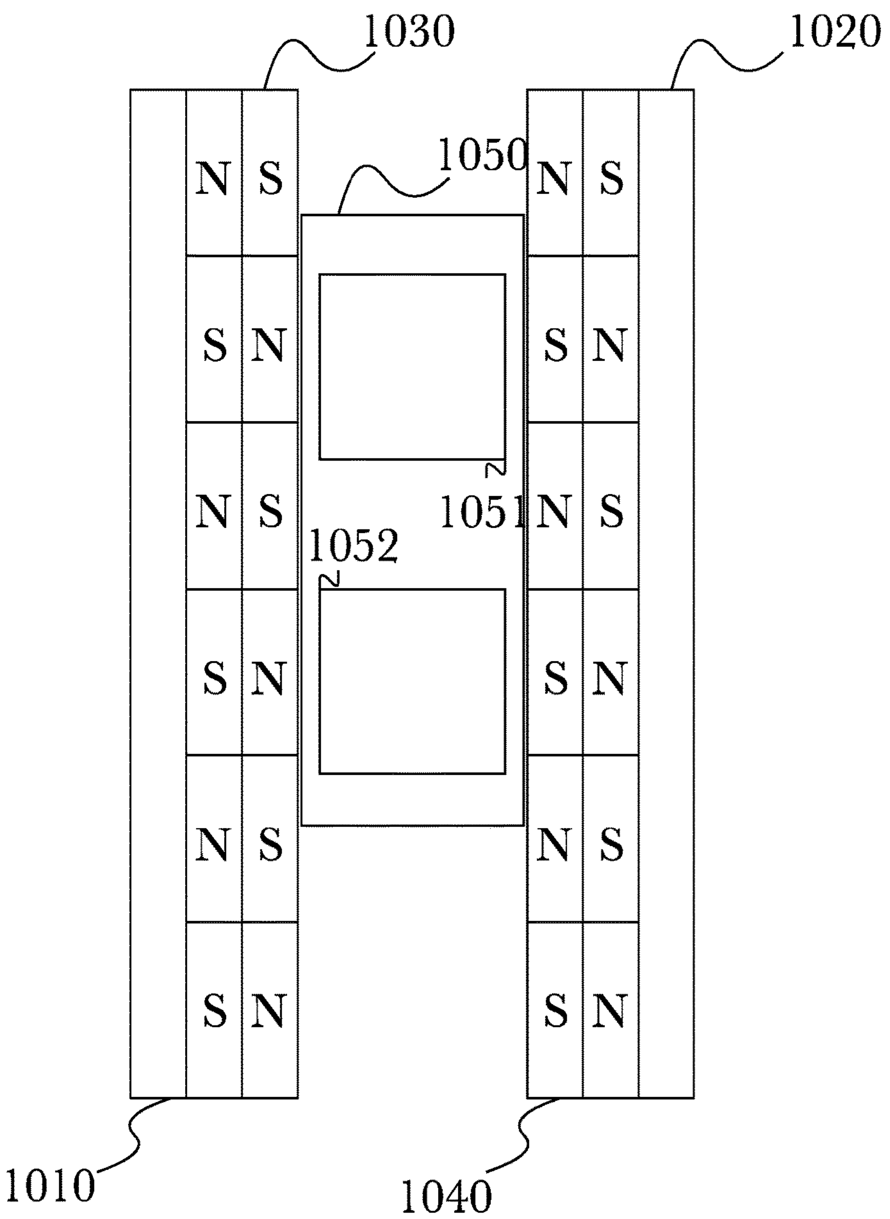
FIG. 10 shows an aspect of an embodiment of male sexual stimulation device comprising linear motor.

FIG. 10 shows an aspect of an embodiment of male sexual stimulation device comprising linear motor. A linear motor has a similar electromagnetic operation to a traditional DC motor, but with the stator 1010-1040 and rotor 1050 being "unrolled," such that linear force is produced instead of rotational force (torque). Shown in this figure is a U-channel synchronous linear motor, with a stator comprising arrays or planes of magnetic pairs 1030, 1040, resting on a substrate 1010, 1020, with a rotor 1050 comprising two coils (wound in parallel to the stators) 1051, 1052 which are mechanically connected, and operate similarly to the coils in a regular motor in that current flowing into the coils (typically through electrical contacts called brushes) allows mechanical motion to be achieved in either direction along the plane of magnets 1030, 1040. Variations of linear motors include alternating-current linear induction motors (LIM) and linear synchronous motors (LSM).

Figure 11:
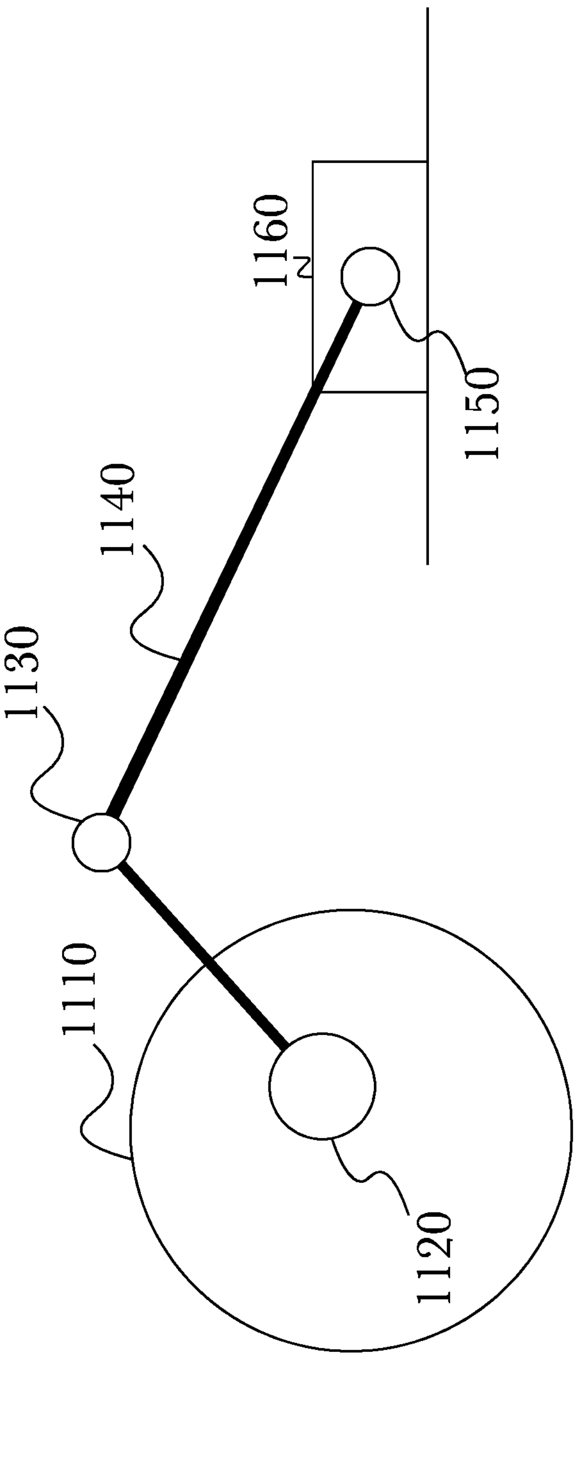
FIG. 11 shows an aspect of an embodiment of male sexual stimulation device comprising slider-crank mechanism.

FIG. 11 shows an aspect of an embodiment of male sexual stimulation device comprising a slider-crank mechanism. An alternative method for linear motion of a gripper or any other component in a male sexual stimulation device may be a slider-crank mechanism, comprising a wheel 1110 which may itself be powered by a built-in motor or by some other motor in a system, a bar-like arm 1140, a connecting wheel 1120 which is smaller than a first wheel 1110, a joint 1130 allowing for the arm 1140 to bend around the joint, an object to push or pull 1160, and a connecting wheel-like joint to the object 1150. As a wheel 1110 is turned, the arm 1140 may be retracted or pushed while still being connected to a wheel-like joint 1120, resulting in force being applied to an object 1160 attached by a joint 1150 to an arm 1140.

Figure 12:
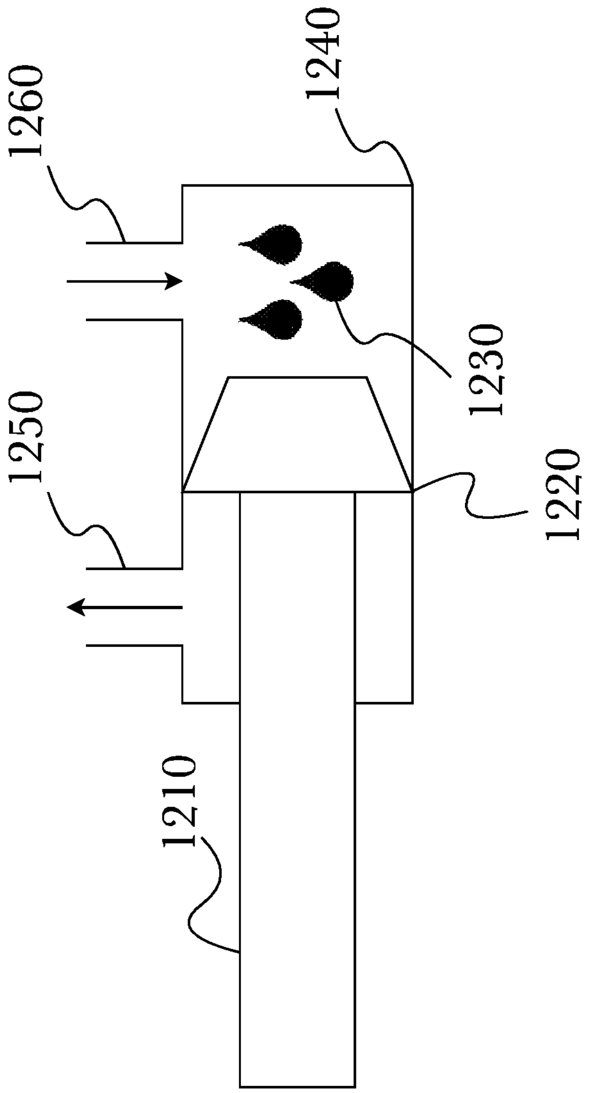
FIG. 12 shows an aspect of an embodiment of male sexual stimulation device comprising hydraulic or pneumatic linear actuator.

FIG. 12 shows an aspect of an embodiment of male sexual stimulation device comprising a hydraulic or pneumatic linear actuator. A piston 1210 exists as part of a pneumatic or hydraulic linear actuator, with a piston head and gasket 1220, actuator body 1240, a retract flow port 1250, extend flow port 1260, and a fluid chamber capable of holding either air, hydraulic fluid, or some other appropriate liquid or gas 1230. By fluid flowing through the extend flow port 1260 into the fluid chamber 1230, pressure is exerted on a piston head and gasket 1220, causing the piston bar 1210 to extend outward as the fluid chamber 1230 fills with fluid. A retraction of the piston bar 1210 may be accomplished by fluid flowing from the retract flow port 1250 into the fluid chamber 1230, causing pressure to build on the opposite side of the piston and gasket 1220, allowing for bi-directional linear motion from such an actuator.

Figure 13:
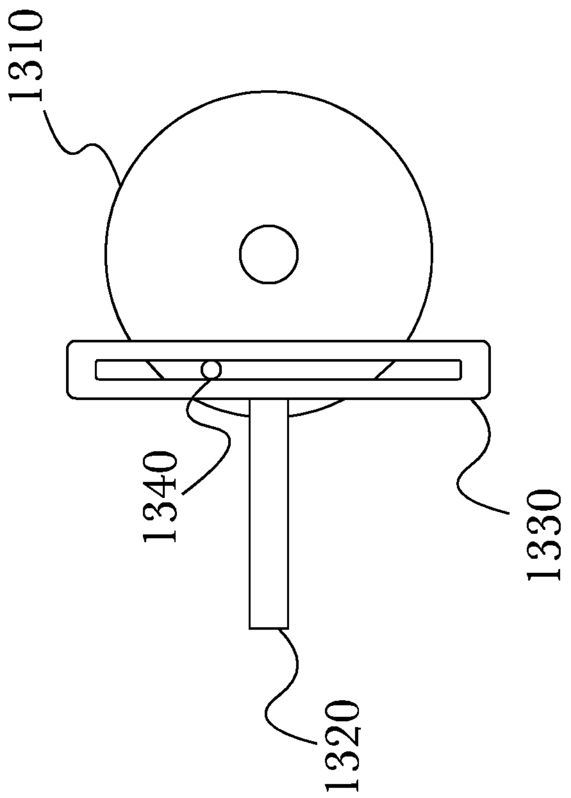
FIG. 13 shows an aspect of an embodiment of male sexual stimulation device comprising a scotch yoke mechanism.

FIG. 13 shows an aspect of an embodiment of male sexual stimulation device comprising a scotch yoke mechanism. A large wheel-like object 1310 holds a yoke 1330 by a connecting object 1340, with a yoke 1330 having a piston 1320 connected, allowing the rotation of the large wheel-like object 1310 to push or pull the yoke 1330 and therefore translate rotational motion into linear motion of a piston 1320.

Figure 14:
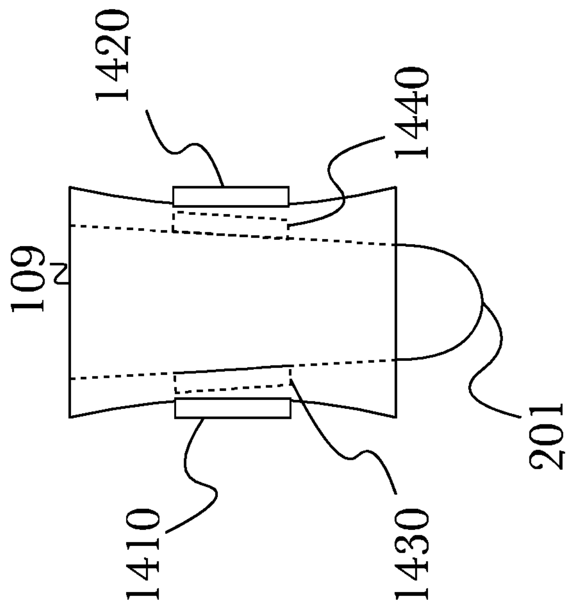
FIG. 14 shows an aspect of an embodiment of male sexual stimulation device comprising a magnetic gripper.

FIG. 14 shows an aspect of an embodiment of male sexual stimulation device comprising a magnetic gripper. According to this aspect, the flexible sleeve 201 is affixed to the gripper by magnets 1410, 1420 which may pair with magnets 1430, 1440 attached to the exterior of an insertable sleeve 201, rather than affixing the sleeve to the gripper mechanically.

Figure 15:
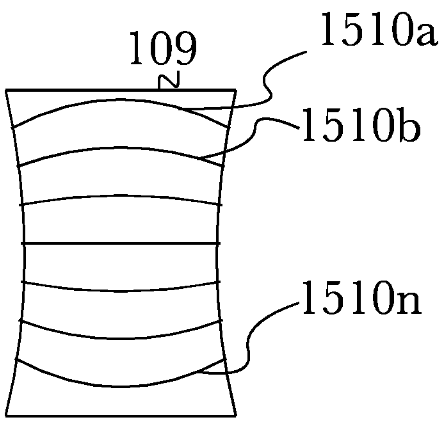
FIG. 15 shows an aspect of an embodiment of male sexual stimulation device comprising a gripper with built-in heating elements.

FIG. 15 shows an aspect of an embodiment of male sexual stimulation device comprising a gripper with built-in heating elements. Heating elements are shown 1510*a-n*, being affixed to a gripper 109, such heating elements allowing a gripper 109 to be warmed to a preset temperature allowing for the sexual stimulation device to be self-heating and thereby more comfortable to users.

Figure 16:
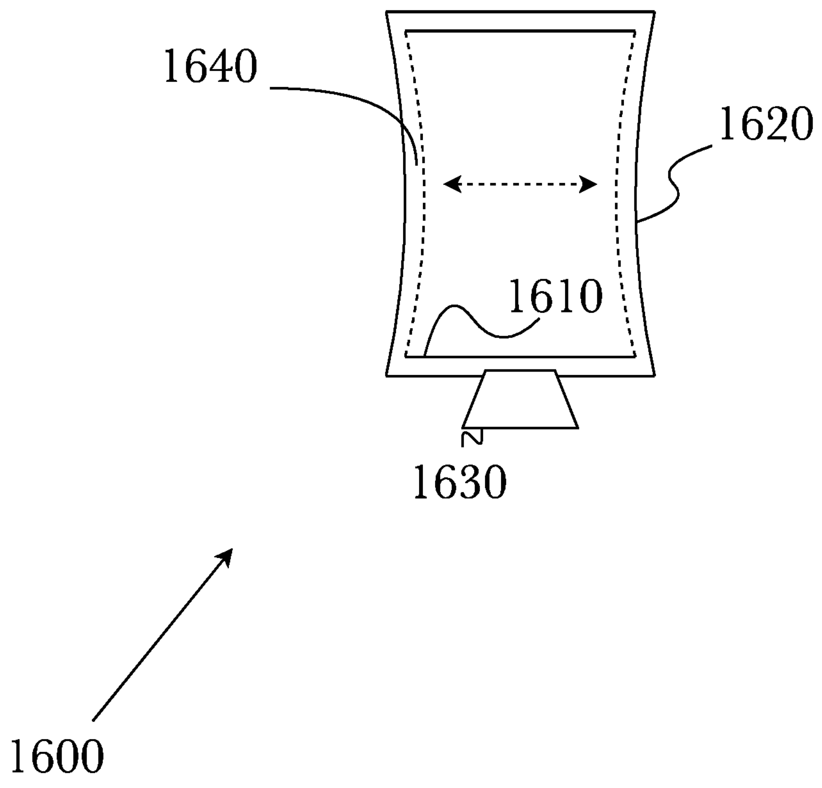
FIG. 16 shows an aspect of an embodiment of male sexual stimulation device comprising an inflatable gripper.

FIG. 16 shows an aspect of an embodiment of male sexual stimulation device comprising an inflatable gripper 1600. According to this aspect, a gripper 1600 is now presented as a volumetric object with a cavity 1640 between an exterior and interior wall 1610, 1620, capable of being filled with either air or some other fluid from a valve 1630, which causes at least a portion of the gripper to expand, allowing adjustment of the size or tightness of the gripper, and allowing a difference in texture and feel versus a rigid gripper. The pressure of a fluid between the walls 1610, 1620 may be adjustable or may be pre-set on item fabrication. A person of ordinary skill in the art will recognize that the inflatable gripper 1600 and cavity 1600 may be of any shape or size, and may be made from any suitable flexible material or (as shown here) a combination of rigid and flexible materials.

Figure 17:
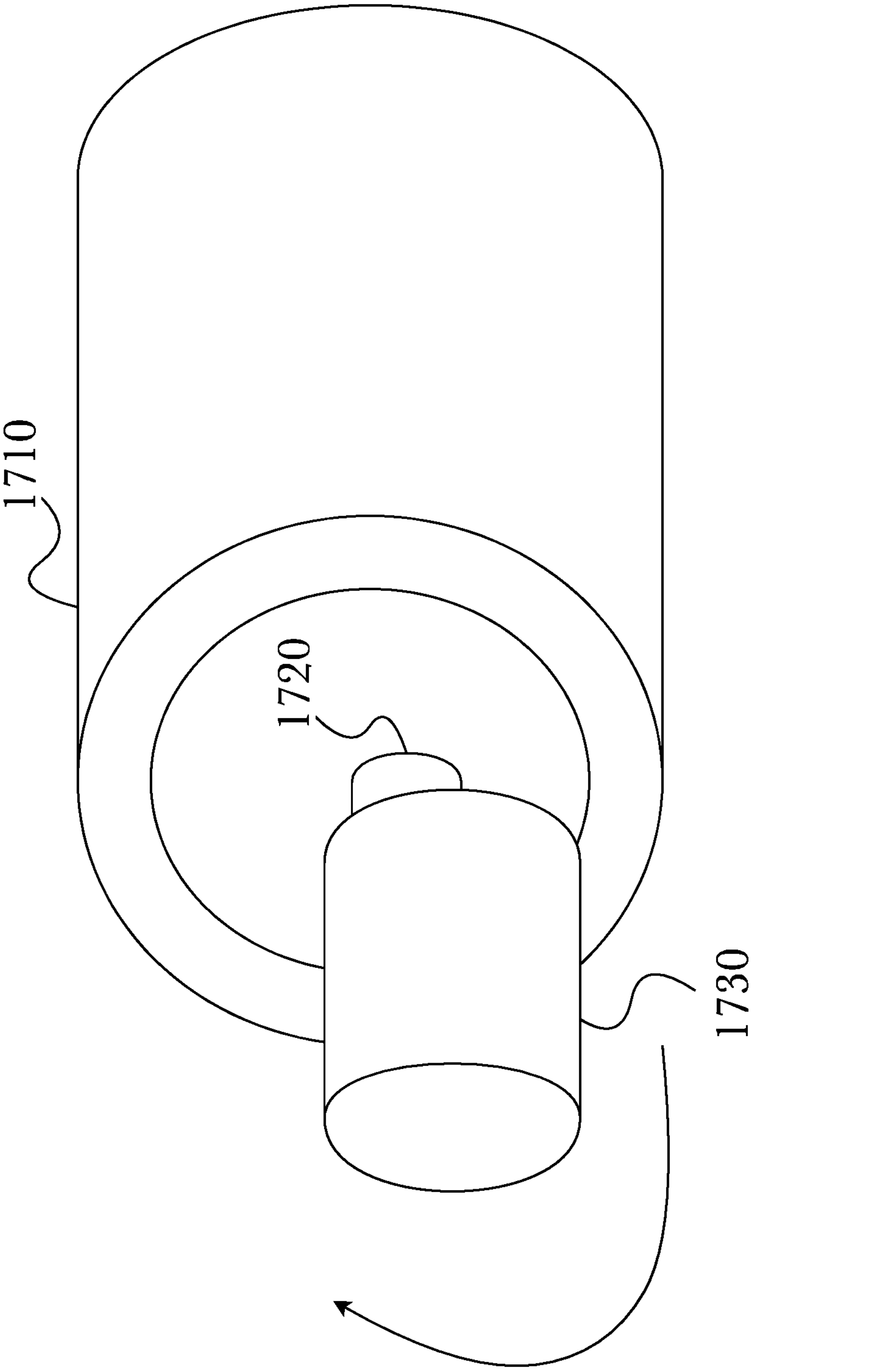
FIG. 17 shows an aspect of an embodiment of male sexual stimulation device comprising a vibrating gripper.

FIG. 17 shows an aspect of an embodiment of male sexual stimulation device comprising a vibrating motor. An exemplary motor 1710 is shown, with an unevenly distributed weight 1730 attached to an externally rotating element 1720, which, when the motor 1710 is activated, rotates generating force due to the unevenness of the weight 1730, allowing for the mechanism to vibrate. A vibrating motor as shown may be used to cause the gripper to vibrate, providing additional stimulation.

Figure 18:
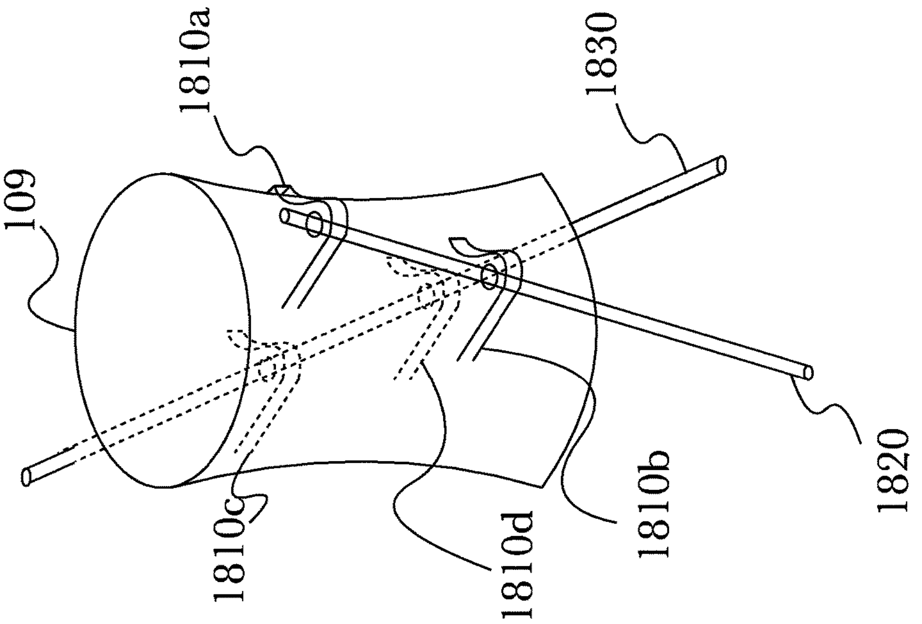
FIG. 18 shows an aspect of an embodiment of a male sexual stimulation device in which rotational motion is used in addition to linear motion.

FIG. 18 shows an aspect of an embodiment of a male sexual stimulation device in which rotational motion is used in addition to linear motion. Shown are four brackets 1810*a-d*, offset from one another and not aligning vertically, such that the gripper is held vertically when inserted onto guide rods 1820, 1830. The guide rods may be configured to be tilted, such that when the gripper 109 is moved up and down on the guide rods 1820, 1830, the gripper 109 partially rotates, providing rotational motion as well as linear motion. Alternate configurations would include guide rods 1820, 1830 formed in a spiral, with brackets 1810*a-d* on the gripper 109 vertically aligned, such that when the gripper 109 is moved up and down on the guide rods 1820, 1830, the gripper 109 partially rotates, providing rotational motion as well as linear motion.

Figure 19:
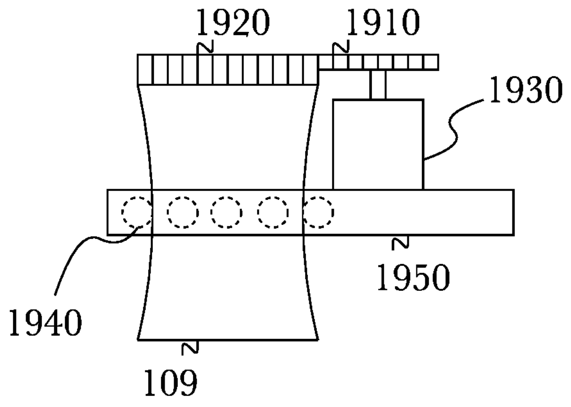
FIG. 19 shows an aspect of another embodiment of a male sexual stimulation device in which rotational motion is used in addition to linear motion.

FIG. 19 shows an aspect of another embodiment of a male sexual stimulation device in which rotational motion is used in addition to linear motion. A motor 1930 is shown, connected to a small gear train comprising two gears 1910, 1920, and providing rotational motion to a gripper 109. A bracket 1950 may hold the gripper 109 in a ball bearing mechanism containing ball bearings 1940 which allows the gripper 109 to rotate under power of the motor 1930 independently of the linear motion of the bracket parallel to the longitudinal axis of the gripper 109. A person of ordinary skill in the art will recognize that any rotational bearing mechanism (e.g., a sleeve bearing) may be used.

Figure 20:
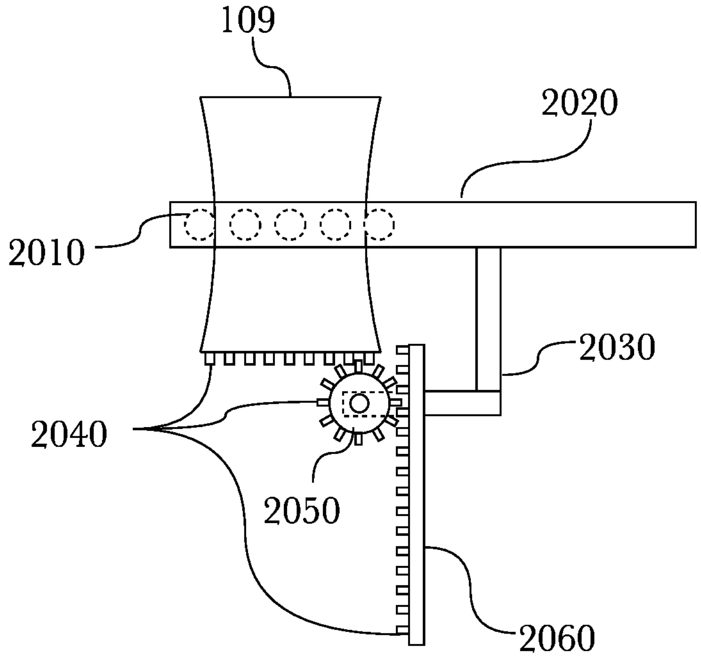
FIG. 20 shows an aspect of another embodiment of a male sexual stimulation device in which rotational motion is used in addition to linear motion.

FIG. 20 shows an aspect of another embodiment of a male sexual stimulation device in which rotational motion is used in addition to linear motion. Shown is a gripper 109, held by a bracket 2020 with a ball bearing mechanism containing ball bearings 2010. A small gear 2050 is also connected to the bracket by an arm 2030. The bottom edge of the gripper 109 contains teeth 2040 that engage with the teeth 2040 of the small gear. The teeth 2040 of the small gear simultaneously engage with the teeth 2040 of a linear rack 2060, which is mounted independently of the gripper/bracket/arm/gear mechanism. This configuration is commonly known as a "rack and pinion" mechanism wherein rotation of one part is translated through a gear into linear motion in another part, and vice-versa. When the bracket gripper/bracket/arm/gear mechanism is moved in a linear up and down motion, the small gear 2050 rotates because of its engagement with the linear rack 2060, causing the gripper 109 to rotate, correspondingly. In this example, the rotation of the gripper 109 is at a fixed rate to the linear motion. A person of ordinary skill in the art will recognize that any rotational bearing mechanism (e.g., a sleeve bearing) may be used.

Figure 21:
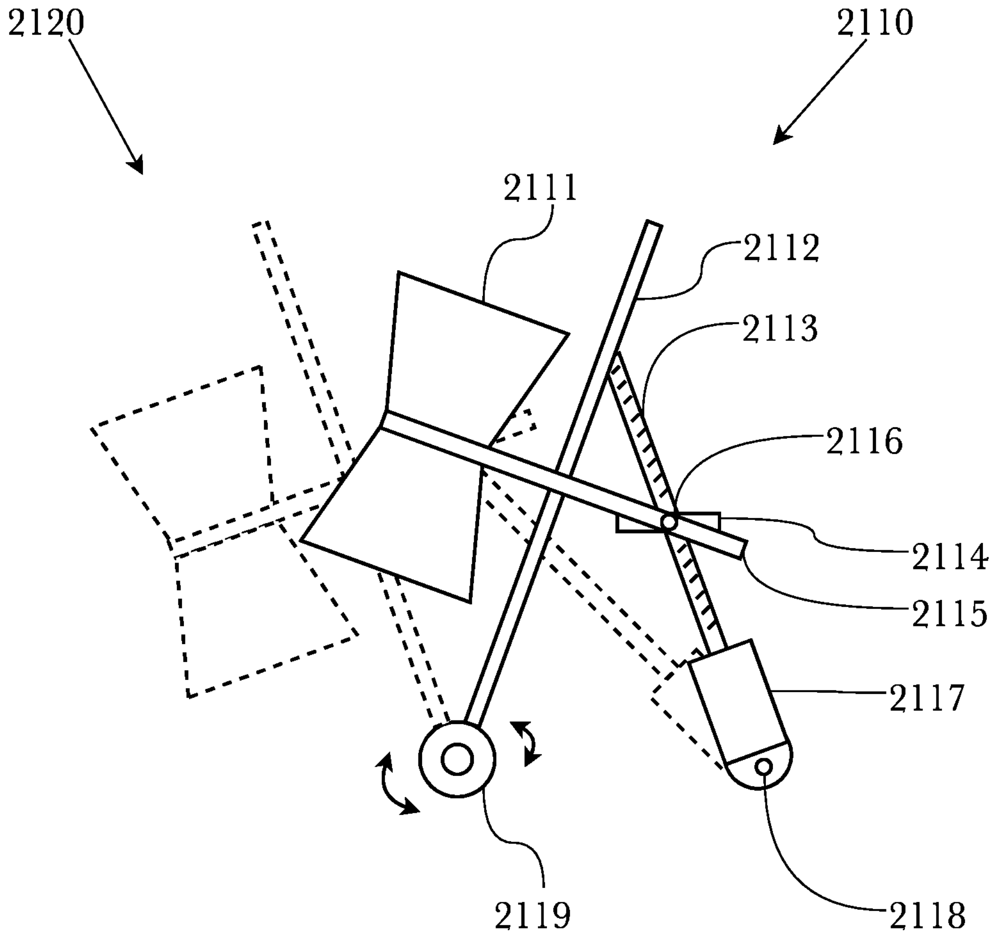
FIG. 21 shows an aspect of an embodiment of a male sexual stimulation device in which the axis of linear motion is movable.

FIG. 21 shows an aspect of an embodiment of a male sexual stimulation device in which the axis of linear motion is movable. The mechanism of this aspect comprises one or more guide rods 2112 which are connected to the device at the bottom using a first pivot 2119. A bracket 2115 is slid onto the guide rods 2112, and a gripper 2111 is attached to the bracket 2115. A motor 2117 is attached to the device with a second pivot 2118. A threaded screw 2113 is attached to the drive shaft of the motor 2117. The screw 2113 is threaded through a pivoting nut 2114, which pivoting nut 2114 is attached via a third pivot 2116 to the bracket 2115. When the motor 2117 is operated to retract the mechanism, the bracket 2114 is pulled down the guide rods and the guide rods/bracket/gripper mechanism is tilted toward the motor 2117, as shown in a first state 2110 of the mechanism. When the motor 2117 is operated to extend the mechanism, the bracket 2115 is pushed up the guide rods 2112 and the guide rods/bracket/gripper mechanism is tilted away from the motor 2117, as shown in a second state 2120 of the mechanism.

Figure 22:
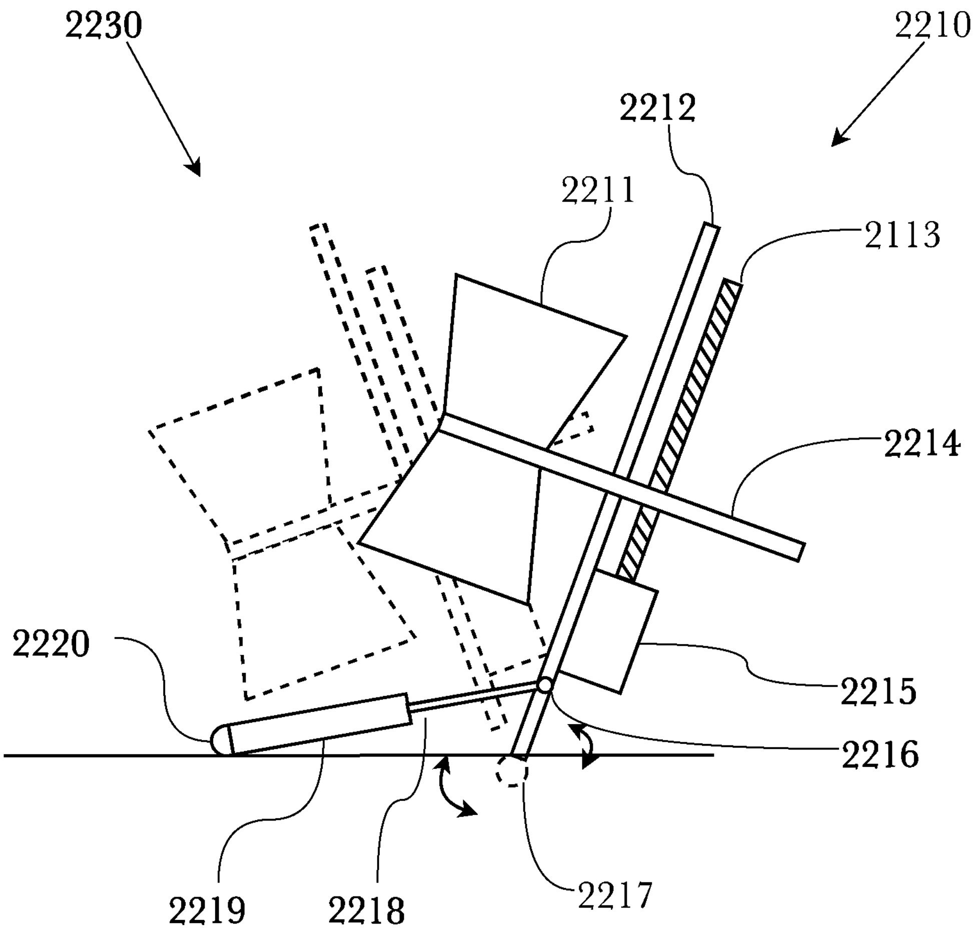
FIG. 22 shows an aspect of another embodiment of a male sexual stimulation device in which the axis of linear motion is movable.

FIG. 22 shows an aspect of another embodiment of a male sexual stimulation device in which the axis of linear motion is movable. The mechanism of this aspect comprises a gripper 2211 designed to grip a removable sleeve, one or more guide rods 2212 onto which the gripper 2211 is mounted, a screw 2213 threaded through a threaded portion of the bracket affixed to a shaft of a motor 2215, which may be utilized to move a gripper 2211 up or down through the use of a connected bracket 2214. There exists further, a first ball-joint 2217 allowing motion in at least two directions along an axis but potentially movement in movement in two axes for possible circular motion, connected to one or more actuators 2219 with an actuator piston 2218 which may be used to tilt the guide rods in one or more directions, independently of the linear motion of the bracket 2214 and gripper 2211. The actuators 2219 are connected to the device with a second ball-joint 2220, and the actuator pistons 2218 are connected to the guide rods 2212 with a pivot 2216. When an actuator 2119 is operated to extend the mechanism, the guide rods 2112 are tilted away from the actuator 2119, as shown in a first state 2210 of the mechanism. When an actuator 2119 is operated to retract the mechanism, the guide rods are tilted toward the actuator 2119, as shown in a second state 2230 of the mechanism.

Figure 23:
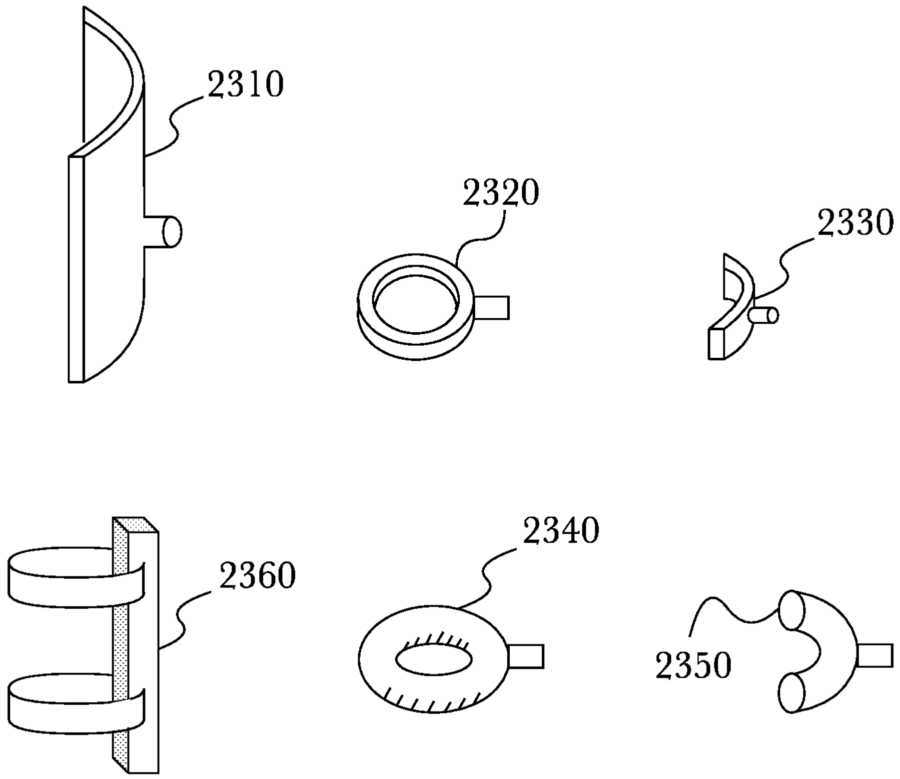
FIG. 23 shows exemplary variations of the gripper aspect of an exemplary male sexual stimulation device.

FIG. 23 shows exemplary variations of the gripper aspect of an exemplary male sexual stimulation device. Possible variations of a gripper may include a partial tube 2310, a ring 2320, a partial-ring 2330, wire or strap loops 2360, a rounded ring 2340, or partial rounded ring 2350. A person skilled in the art will recognize that other variations may be possible.

Optionally, the device may include a number of other functions to enhance the user experience. For example, a grippable surface may be molded to the outside of the housing to provide better grip in the hand. The device may contain the ability to warm the sheath to an optimal temperature prior to and during use. The device may also contain additional methods of stimulation in addition to the primary linear motion, such as suction, vibration, or direct electrical stimulation. The device may be made more portable by designing it to operate from batteries contained within the device housing. It will be apparent to one skilled in the art, that the linear motion could be generated by some other means than a rotary electric motor.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

What is claimed is:

1. A male sexual stimulation device comprising:

a reciprocating linear motion driver;

a gripper attached to the reciprocating linear motion driver; and a flexible sleeve which is inserted into the gripper and which has a means for affixing the sleeve to the gripper, wherein a penis may be inserted into the flexible sleeve and remain fully inserted inside the device during stimulation, and wherein, when the device is activated, the inserted penis remains immobile inside the device while the gripper moves at least a portion of the sleeve affixed to the gripper in an axial reciprocating linear motion along the penis, providing sexual stimulation through friction of the interior of the sleeve against the penis contained in the sleeve due to the axial reciprocal linear motion of the gripper and the portion of the sleeve affixed to the gripper.

2. The device of claim 1, wherein the linear motion driver comprises a motor and screw mechanism.

3. The device of claim 2, wherein the screw mechanism is a threaded ball screw.

4. The device of claim 2, wherein the screw mechanism is a threadless ball screw.

5. The device of claim 1, wherein the linear motion driver comprises a belt-driven linear actuator.

6. The device of claim 1, wherein the linear motion driver comprises a linear motor.

7. The device of claim 1, wherein the linear motion driver comprises a slider-crank.

8. The device of claim 1, wherein the linear motion driver comprises a hydraulic linear actuator.

9. The device of claim 1, wherein the linear motion driver comprises a pneumatic linear actuator.

10. The device of claim 1, wherein the flexible sleeve and gripper each comprise magnets, and the flexible sleeve is affixed to the gripper by magnetic attraction.

11. The device of claim 1, wherein the gripper further comprises a heating apparatus that warms the flexible sleeve to an optimal temperature.

12. The device of claim 1, wherein the gripper comprises an inflatable cavity that may be filled with a gas or a fluid.

13. The device of claim 1, wherein the gripper comprises a vibration mechanism that provides stimulation in addition to the linear motion stimulation.

14. The device of claim 1, further comprising one or more guide rods that guide the linear motion, the one or more guide rods being configured such that each travel along the one or more guide rods causes the gripper to partially rotate about a longitudinal axis parallel to the linear motion.

15. The device of claim 1, further comprising a motor or actuator attached to the gripper mechanism and configured to rotate the gripper about a longitudinal axis parallel to the linear motion independently of the linear motion.

16. The device of claim 1, further comprising a rack and pinion mechanism configured to rotate the gripper about a longitudinal axis parallel to the linear motion as it travels in a linear motion.

17. The device of claim 1, further comprising:

one or more guide rods that guide the linear motion; and a pivot or joint installed at the bottom of the one or more guide rods near the end of the device where a penis may be inserted;

where the linear motion driver has a pivot at the bottom and is affixed at an angle to the guide rods such that the linear motion causes the one or more guide rods to tilt at the pivot, changing the direction of the linear motion during the linear motion along the one or more guide rods.

18. The device of claim 1, further comprising:

one or more guide rods that guide the linear motion;

a pivot or joint installed at the bottom of the one or more guide rods near the end of the device where a penis may be inserted; and a separate motor, driver, or actuator which changes the pivot angle of the one or more guide rods independently of the linear motion;

wherein the linear motion driver is affixed to the guide rods such that the linear motion remains parallel to the guide rods as the guide rods tilt.

* * * * *